United States Patent [19]

Johnson

[11] 4,009,005
[45] Feb. 22, 1977

[54] APPARATUS FOR RADIOIMMUNOASSAY WITH REGENERATION OF IMMUNADSORBENT

[75] Inventor: Lavell R. Johnson, Salt Lake City, Utah

[73] Assignee: Becton, Dickinson and Company, East Rutherford, N.J.

[22] Filed: Apr. 7, 1975

[21] Appl. No.: 565,850

Related U.S. Application Data

[63] Continuation-in-part of Ser. No. 342,513, March 19, 1973, Pat. No. 3,896,217.

[52] U.S. Cl. .................................. 23/253 R
[51] Int. Cl.² ................ G01N 31/06; G01N 33/16
[58] Field of Search .............. 23/253 R, 259, 230.3, 23/230.6

[56] References Cited

UNITED STATES PATENTS

| | | | |
|---|---|---|---|
| 3,519,390 | 7/1970 | Dickey et al. | 23/230.6 |
| 3,607,073 | 9/1971 | Stamm | 23/253 R X |
| 3,788,812 | 1/1974 | Dupre | 23/230.6 |
| 3,793,445 | 2/1974 | Updike et al. | 23/230.6 |
| 3,806,321 | 4/1974 | Durrum et al. | 23/253 R |
| 3,814,581 | 6/1974 | Reunanen | 23/253 R X |

OTHER PUBLICATIONS

Chem. Abstr., vol. 74:123000K (1971).
Chem. Abstr., vol. 75:33018p (1971).
Updike et al., Clin. Chem., vol. 19, pp. 1339–1343 (1973).
Akanuma et al., Biochem. Biophys. Res. Comm., vol. 38, pp. 947–953 (1970).

*Primary Examiner*—Morris O. Wolk
*Assistant Examiner*—Timothy W. Hagan
*Attorney, Agent, or Firm*—Mario A. Martella

[57] ABSTRACT

Apparatus for radioimmunoassay provides a continuously reusable short cycle analytical system of particular use in biochemical analysis such as the determination of steroids, hormones, polypeptides, viruses, vitamins, drugs, and the like. The apparatus disclosed samples a mixture of an unlabelled antigen sample and a known concentration of labelled antigen, bringing the mixture into contact with a mass of appropriate antibody that has been immobilized thereby to bind at least part of the mixed antigen to the antibody. The amount of bound and/or unbound labelled antigen is detected and counted and, by use of previously prepared standards, the unknown concentration of unlabelled antigen is found. The still immobilized antibody is regenerated for immediate reuse by rinsing it with a selected eluting solution that is capable of breaking the antigen-antibody. Alternate ways of immobilizing the antibody are described. Several suitable eluting solutions are disclosed. Also disclosed is a novel apparatus by which immunoassay may be automatically carried out and the antibody reused many times. By proper substitution, the antibody and antigen may be reversed.

22 Claims, 5 Drawing Figures

APPARATUS FOR RADIOIMMUNOASSAY WITH REGENERATION OF IMMUNADSORBENT

This is a continuation-in-part application of Ser. No. 342,513, which was filed on Mar. 19, 1973, now U.S. Pat. No. 3,896,127.

BACKGROUND OF THE INVENTION

1. Field of the Invention

This invention relates generally to the analytical technique known as radioimmunoassay in which antigens are bound to specific antibodies and, through the use of tracers (labels) and predetermined behavior standards the concentration of antigen in a sample is determined. More particularly, the invention relates to improved apparatus for radioimmunossay in which a short-cycle time, hence more rapid analysis is achieved, the antibody mass (immunoadsorbent) is regenerated to be reused indefinitely rather than being wasted and the entire operation is automated.

2. State of the Art

Radioimmunoassay is an analytical technique which depends upon the competition (affinity) of antigen for antigen-binding sites on antibody molecules. In practice, standard curves are constructed from work on a plurality of samples each containing (a) the same known concentration of labelled antigen, and (b) various, but known, concentrations of unlabelled antigen. Antigens are labelled with a radioactive isotope tracer. The mixture is incubated in contact with an antibody, the free antigen is separated from the antibody and antigen bound thereto, and then, by use of a suitable detector, such as a gamma or beta radiation detector, the percent of either the bound or free labelled antigens is determined. This procedure is repeated for a number of samples containing various known concentrations of unlabelled antigens and the results plotted. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In actual analysis, the sample in which the concentration of antigen is to be determined is mixed with a known amount of tracer antigen. Tracer antigen is the same antigen known to be in the sample but which has been labelled with a suitable radioactive isotope. The sample with tracer is then incubated in contact with the antibody. Thereafter, it may be counted in a suitable detector which counts the free antigen remaining in the sample. The antigen bound to the antibody or immunoadsorbent may also be similarly counted. Then, from the standard curve, the concentration of antigen in the original sample is determined. Afterwards, the antibody or immunoadsorbent mass is discarded.

In order to detect the percentage of antigen that is bound to the antibody (bound antigen) and/or the percentage that remains free or unbound it is necessary to first separate the sample into a fraction containing bound antigen and one containing only free antigen. One common method for doing this is to add a dextran coated charcoal to the mixture. The charcoal is allowed to adsorb the free antigen. The charcoal with adsorbed free antigen is then separated from the antibody (and bound antigen) by centrifugation. Another known procedure is to add to the mixture another antibody which selectively precipitates the first antibody (with the bound antigen) thus leaving in solution only free antigen. Classification into appropriate free and bound fractions is then effected by separating the precipitate from the supernatant by centrifugation or other suitable means. Some workers have resorted to the technique of binding the antibody to the inner walls of a plastic vessel, filling the vessel with the antigen bearing sample, allowing it to stand for an incubation period that typically ranges from 4 to 72 hours and then separating free antigen from bound antigen by draining and rinsing the vessel leaving therein only the antibody and bound antigen. A more recently developed technique is to prepare the immunoadsorbent by binding the antibodies onto an insoluble cross-linked dextran. The immunoadsorbent and antigen bearing sample are incubated then the dextran with bound antigen is separated from the solution by suitable means.

In all of the foregoing procedures, the percentage of labelled antigen in either or both the bound or free fractions is determined and the standard curve used to determine the antigen concentration. Thereafter, the immunoadsorbent is discarded.

Although the foregoing radioimmunoassay techniques have proven to be valuable tools and have gained widespread acceptance, they are still not all that are to be desired because the antibody (immunoadsorbent) is consumed with each analysis hence must be discarded. Moreover, prior practice is batch type and the several reagents are added to the antibody in test tubes in which the separate steps, such as incubation, rinsing and the like, are performed, thus resulting in a slow and costly operation.

SUMMARY OF THE INVENTION

The present invention provides improved apparatus for carrying out radioimmunoassay. In accordance with the invention the immunoadsorbent (antibody) is repeatedly and rapidly regenerated thus obviating the need and therefore the time and cost of constant replacement. According to the invention, apparatus is provided by which the method may be carried on continuously in constantly repeating cycles thereby eliminating the expensive time-consuming batch operation. A novel equipment arrangement for automating the method is also provided.

The invention is predicted on the discoveries that (1) by forming the immunoadsorbent mass as an immobilized mass of antibodies through which the antigen sample and other reagents may flow the procedure may be sequentially carried out without resort to the use of several manual steps and (2) the immobilized immunoadsorbent may be regenerated for repeated reuse by the rinsing with a solvent or eluting solution having particular characteristics. That is to say, bound antigens are released so that the antibody may be washed clean of bound antigen and thereby regenerated for reuse without affecting the essential characteristic of the antibody mass such as its ability to permit repeated flow of antigen solution therethrough and its antigen-binding efficiency during a large number of cycles.

As used herein, the term immobilized antibody mass refers to a mass of antibodies held in place in a liquid stream flow path in such a manner that the stream may flow over or through the mass while the latter remains in place.

A suitable antibody mass may be formed from solid surfaces such as glass or water insoluble polymers to which the antibodies are attached by covalent bonds. A mass of such beads with attached antibodies is supported on a screen in a tube or other hollow column through which the antigen bearing sample and other reagents are flowed sequentially. An improved immobilized antibody mass is described in Application Ser. No. 342,513, filed Mar. 19, 1973 now U.S. Pat. No. 3,896,217, and assigned to the same assignee. Covalent coupling of antibodies or antigens to said carrier is known. (It is disclosed for instance in U.S. Pat. No. 3,652,761).

In accordance with this invention, antibodies, specific to the antigen under analysis, are covalently coupled to a solid support such as beads, a mass of the beads is immobilized, an antigen bearing solution is flowed therepast, the percentage of free labelled antigen remaining in the solution is detected, the bound antigen is released simultaneously with regeneration of the antibody mass and the percentage of released antigen is also detected. The percentages are determined with reference to the total antigen in the incoming sample. As noted, detection is of the tracer of labelled antigen.

Release of bound antigen and concomitant regeneration or reactivation of the antibody mass is effected by rinsing it with a solvent or eluting solution that breaks the bond between antigen and antibody, but does not break the covalent bond between the antibody and its support. Moreover, the solvent must not alter either the flow characteristic or antigen affinity of the antibody mass.

Another type of immobilized antibody mass can be formed by encapsulating antibodies in a semi-permeable membrane. A quantity of such micro-capsules is then held in place in a column through which the antigen-bearing solution flows. The membranes are selected to block the outward passage of antibodies while permitting the free passage of antigens and their solvent in both directions.

In the case of membrane capsules, since there is no covalent bond, there is no need to be concerned with its destruction by the regenerating solvent. However, the limitation must still be observed that the solvent not adversely affect the flow characteristic or adsorption efficiency of the antibody. It is possible to increase efficiency of the membranes by coupling the antibodies to a soluble polymer thereby increasing the molecular weight of the combined antibody thus enabling the use of a relatively more permeable membrane.

In connection with flow characteristics in either system, the solvent should not cause swelling of the antibody support or the membrane wall to the point where flow of relatively small antigens is blocked or the loss of relatively larger antibodies through the wall occurs.

In summary then, the invention comprises apparatus for carrying out the steps of providing a mass of immobilized specific antibodies to selected antigen, holding such mass in a liquid flow path, preparing an antigen bearing sample by adding a known quantity of labelled antigen to a sample containing an unknown amount of the same antigen, flowing such sample along said liquid flow path over and in contact with said immobilized antibody, thereafter detecting the quantity of free labelled antigen remaining in the sample and/or that which is bound to the antibody.

The quantity of antigen bound to the antibody is determined by rinsing the antibody with a particular solvent to release bound antigens then detecting the antigens in the rinse solution.

The solvents found to meet the requirements of this invention have been both hydrophilic and hydrophobic in character. Typical solvents are methyl, ethyl and isopropyl alcohols as well as dimethylformamide.

In it most essential form, the apparatus of this invention comprises a contact chamber having an inlet and outlet and adapted to accommodate the flow of liquid stream therethrough, a mass of antibodies, means for immobilizing said antibodies and holding them in position in said contact chamber in the path of antigen flow therethrough, a detection chamber having an inlet and outlet, a detector associated with said chamber for determining the quantity of a given tracer flowing through the said chamber, conduit means for conducting liquid from the outlet of said contact chamber to the inlet of said detection chamber, a source of sample solution containing both labelled and unlabelled antigen, a source of regenerating solvent, means for supplying separately and sequentially to the inlet of said contact chamber for flow therethrough a quantity of said sample and of said solvent, and means for controlling the flow of said sample and solvent through said contact chamber and said detection chamber. Means are also provided for introducing a so-called scintillation cocktail into the system between the contact chamber and detector to flow through the latter and therein to convert radioactive decay impulses to light or photons for detection by a photo multiplier detector.

The required flow rates through the contact chamber and detector are determined emperically and are controlled by metering pumps. The flow sequence is controlled by valves. By proper timing the flow through the system may be continuous with the rates being selected to provide sufficient time at each station to achieve the results, such as binding, releasing or counting, sought at each station.

In order that the invention may be more readily understood and carried into effect, reference is made to the accompanying drawing and the description thereof which are offered by way of illustration and not in limitation of the invention, the scope of which is defined by the appended claims and equivalents thereof rather than by any illustrative description.

BRIEF DESCRIPTION OF THE DRAWINGS AND DESCRIPTION OF PREFERRED EMBODIMENT

Figure 1:
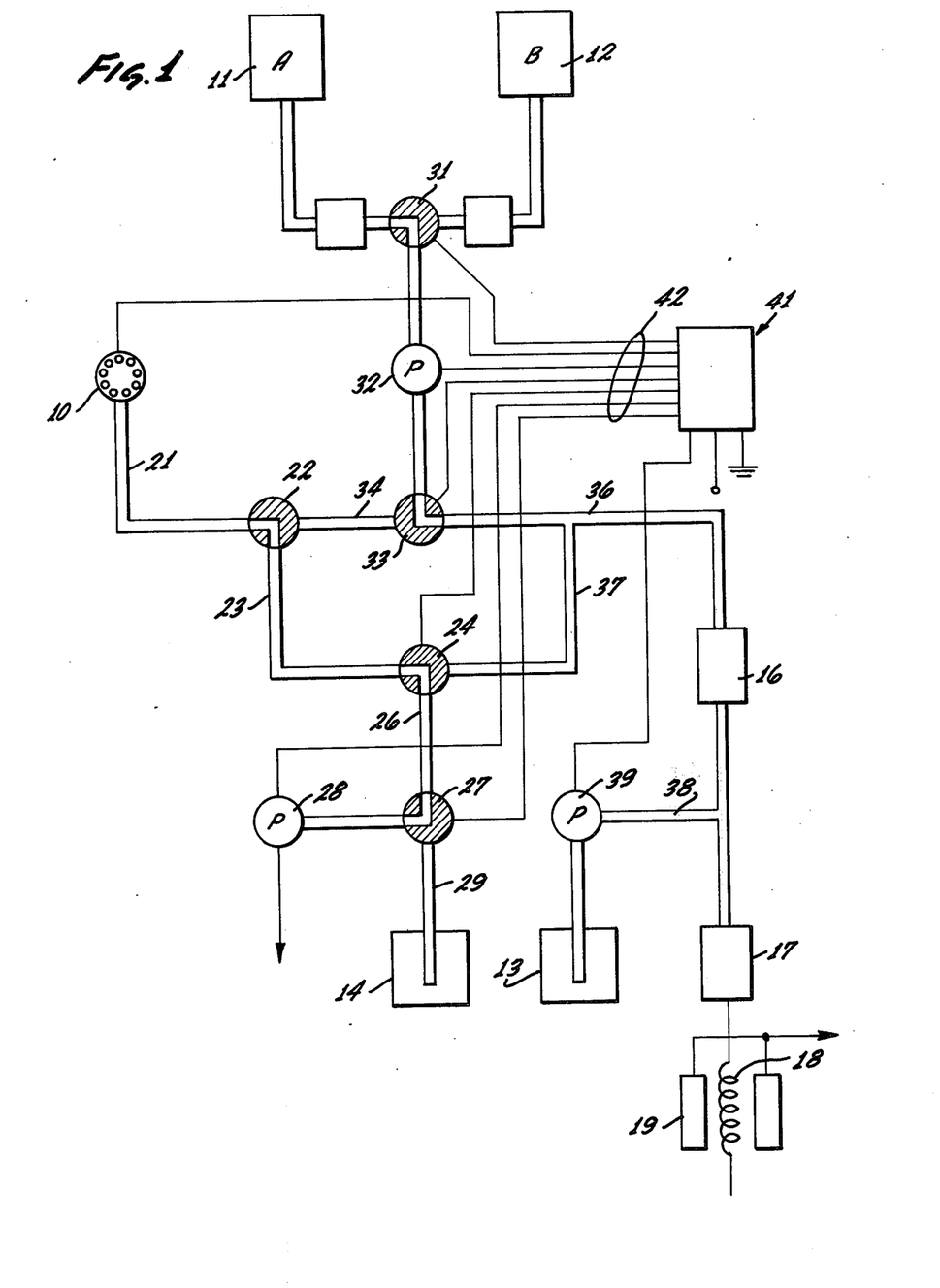
FIG. 1 is a schematic diagram of apparatus embodying the invention.

As illustrated, the system comprises a sample source 10, a source 11 of buffer rinse, a source 12 of regenerating solvent, a source 13 of scintillation cocktail, a rinse water reservoir 14, a contact chamber 16 filled with water reservoir 14, a contact chamber 16 filled with immobilized antibodies (immunoadsorbent) a mixing chamber 17, and a detector chamber or coil 18 with detector 19 adjacent thereto. The foregoing components are connected together by a series of conduits and flow directing valves which, together with metering pumps and a timing mechanism, regulate flow through the system.

Specifically, the sample source 10 connects via a conduit 21 to a two-position valve 22 which in one position connects to a sample loop 23. The sample loop terminates in a two-position valve 24 which in one position connects to a conduit 26 leading to another two-position valve 27 which in one position connects the conduit 26 and sample loop 23 to an aspirator pump 28 which discharges to waste. A rinse water inlet conduit 29 also connects to the pump 28 via the alternate position of valve 27 to keep the pump primed and rinsed when it is not drawing sample.

The displacement rinse flows from tank 11 to a two-position valve 31 which in one position connects through a pump 32 to a further two-position valve 33 whence it connects either to a conduit 34 leading to the valve 22 and sample loop 23 or to a conduit 36 leading to the contact chamber, mixer and detector. A conduit 37 connects the valve 24 to the main conduit 36. A branch conduit 38 connects to the main conduit 36 at a junction between the contact chamber and the detector at a location ahead of the mix chamber 17. A pump 39 is provided to move a reagent from the tank 13 through the conduit 38.

A central timer, generally designated 41, is employed to control sequencing of the valves and pumps. The timer may be custom assembled for the job in accordance with available technology hence, its structure need not be described in detail. It is sufficient to indicate, as is done in the drawing, that the valves, all of which are electrically actuatable solenoid valves, and the metering pumps, all of which are electric, are connected to the timer by suitable conductors 42.

OPERATION OF THE SYSTEM

At the start of a cycle rinse reagent from the tank 11 passes through valve 31, pump 32, valve 33 into and through conduit 36. This rinses the system. Sample from tank 10 is drawn by pump 28 through the valves into and through the sample loop 23 until the loop is rinsed and filled whereupon the valves 22, 24, 27, and 33 switch to the alternate positions whereupon there is a continuous flow from tank 11 through valve 31, pump 32, valve 33, valve 22, loop 23, valve 24 and conduit 37 to conduit 36. Liquid flowing from tank 11 thus displaces sample from the loop into and through the contact chamber 16. When the flow has continued long enough to displace all sample from the loop, the valves 22, 24 and 33 return to the initial positions shown in the drawing. This isolates the sample loop.

After the sample has passed through the contact chamber 16 and the detection coil, the valve 31 shifts to accept regenerating solvent from the tank 12 and directs it through pump 32 and valve 33 directly into conduit 36 to flow through the contact chamber where it releases the bound antigens and carries them to the mixer and detector. Simultaneously, the immunoadsorbent in the contact chamber is regenerated.

The scintillation cocktail in tank 13 typically comprises a primary scintillator, a secondary scintillator and a solubilizer all carried in toluene. Its function is to mix with the antigen bearing solution in the mix chamber 17 and then to convert the radioactive impulses of the tracer to light or photons which can be detected by a photo multiplier detector. Photons may be detected by either a gamma or beta scintillation spectrometer.

The tracer or label is selected from those conveniently available. A label of $^3$H Tritium may be used with a beta scintillator detector with a coincidence circuitry counter whereas an Iodine label $^{125}$I may be used with a gamma detector which does not require the coincidence circuitry. In the tests reported herein, a tritium label was used.

It is important that the sample loop be kept uncontaminated with the regenerating solvent since traces of that mixed with the sampler could reduce the bonding efficiency in the contact chamber.

Although a very elemental sample is illustrated, it will be appreciated that several sophisticated samplers are readily available that may be adapted to use in this invention.

A series of basic tests were performed to confirm that immunoadsorbents when formed as immobilized antibodies could be consistently regenerated with suitable reagents.

Reagents used were as follows:
Buffer Rinse (Solution A)
  0.02 M sodium phosphate, pH 7.5
  0.05 M sodium chloride
  0.01% merthiolate
  0.02% sodium azide
Regenerating solvent (Solution B)
  Solution A with the addition of 30% (v/v) of 95% ethyl alcohol.
Scintillating Solution (Solution C)
  Five parts of a solution of
    0.4% (w/v) 2.5 diphenyloxazole
    0.008% (w/v) 1, 4-bis-2(4-methyl-5-phenyloxazolyl)benzene
    toluene as solvent
  one part of
    Scintisol-GP (manufactured by Isolab, Inc.)

EXAMPLE I

A contact chamber was prepared from a glass pipette plugged at one end with glass wool. A slurry of 0.04 ml of immunoadsorbent suspension was introduced. The suspension contained 20 mg/ml of solid support to which testosterone antibody had been covalently bonded. The chamber was washed with 5 ml of a buffer rinse (Solution A) then by 1 ml of regenerating solvent (Solution B.) The cycle was repeated several times. Each fraction discharged from the contact chamber was separately collected in scintillation vials mixed with 15 ml of scintillation cocktail (Solution C) and counted for 5 minutes in a scintillation spectrometer. The results are shown in Table 1 in which for each of four cycles the percent of bound antigen and percent of free antigen are tabulated. In the case of the bound antigen, it was first released from the immobilized antibody by the regenerating solvent then it was detected and counted.

TABLE I

| | (Sample - $^3$H-Testosterone) | | | |
|---|---|---|---|---|
| | Cycle 1 | Cycle 2 | Cycle 3 | Cycle 4 |
| Percent free* Labelled Antigen | 61.3 | 33.4 | 33.1 | 33.3 |
| Percent Bound** Labelled Antigen | 40.3 | 65.3 | 70.5 | 71.4 |

The first two cycles were used to stabilize conditions.
*Measured after passage through the immobilized antibody.
**Measured after release from the immobilized antibody by the regenerating solvent (Solvent B).

EXAMPLE II

A separate series of tests were conducted on estriol antigen under conditions comparable to those reported in Example I. The data reported in Table II establishes that the antibody may be regenerated many times without loss of efficiency. In the tests, a standard sample always contained 0.28 ng/ml of labelled antigen (62.nC/ml of tritium) plus a known amount of unlabelled estriol. The concentration in the first column recites only the known labelled estriol concentration.

TABLE II

| Conc. Unlabelled Estriol ng/ml | Number of Cycles | Average Percent Bound** | Standard Deviation |
|---|---|---|---|
| 0 | 13 | 84.8 | 0.57 |
| 0* | 22 | 84.6 | 1.02 |
| 0.27 | 5 | 77.1 | 1.1 |
| 0.54 | 14 | 70.6 | 2.2 |
| 1.08 | 10 | 57.3 | 1.1 |
| 2.7 | 13 | 36.1 | 1.9 |
| 5.4 | 8 | 24.3 | .47 |

*These two series were separated in time.
**The bound fraction was measured after release by the regenerating solvent.

All runs were made on a single antibody mass. Twenty-one actual clinical samples were run through the same mass, interspersed among the runs reported in Table II. Additionally, several hundred more standards and other samples were run through the same antibody mass so that it has actually been regenerated about 500 times without detrimental loss in antigen binding efficiency. The tests reported in connection with Table II were all run on the operating prototype hereinafter described in Example III.

A variety of regenerating solvents have been tested and found satisfactory for release of bound antigen and regeneration of antibody. Some solvents, particularly ethyl and isopropyl alcohols, have demonstrated almost indefinite regeneration capacity. In fact, as noted with Solution B, an antibody mass has been regenerated about 500 times. The required characteristics of the solvent are that it breaks the antibody-antigen binding efficiency of the antibody. In practice it will be necessary empirically to determine the proper solvent for any given system.

EXAMPLE III

A prototype system was constructed which employed a turntable sampler holding a plurality of samples and having a lifter for moving the sample tube 21 into and out of samples as they are sequentially rotated into position by a timer. A cyclic timer 41 was employed. A commercially available rotary sample valve was used to perform the functions of valves 22, 24, and 33 in response to signals from the timer. The valves 27 and 31 were simple two-position electrically operated valves. Suitable metering pumps 28, 29, and 32 were used. Flow lines were small bore Teflon plastic tubes typically of 0.0012" to 0.0062" I.D. The contact chamber consisted of a polypropylene tube 0.125" inside diameter by 0.188" long. As used, the columns contained 0.04 ml of a Sephadex G-25 suspension at a concentration of 20 mg Sephadex/ml of a solution of 0.02M sodium phosphate at pH 7.5, 0.05 M NaCl, 0.01% merthiolate and 0.02% sodium azide. Antibody to the antigen was covalently bonded to the Sephadex. The sample loop 23 had a capacity of 0.2 ml.

Flow rates were:
Through the sample loop — 0.45 ml/minute for two minutes
From tank 11 or 12 via pump 32 — 0.112 ml/minute
From tank 13 via pump 39 — 1.0 ml/minute The coil forming the detector cell has a volume capacity of 2.2 ml. The mixer 17 has a capacity of approximately one ml. Detection and counting was accomplished by means of a beta scintillation detector adjacent the coil and coupled to a counter not shown but which is a conveniently available type.

The immunoadsorbent in the contact chamber was an antibody coupled to Sephadex beads which were in turn immobilized in the contact chamber by nylon screen (325–400 mesh). Sephadex is a cross-linked dextran made by Pharmacia A.B. of Uppsala, Sweden. Such beads or other particulate solids with the ability to hold antibodies by covalent bonds make convenient supports on which to bind the antibodies for immobilization.

As previously mentioned the tests reported in connection with Table II were all run in apparatus of the foregoing type.

In operation, a typical total cycle time for some tests was 28 minutes. This total includes a three minute rinse cycle during which rinse from tank 11 flushed the system free from regeneration solvent. The sample loop, which does not require preliminary rinse, is at the same time flushed and filled with sample. The first three minute period is followed by a ten minute period during which reagent from tank 11 flows through the sample loop displacing sample therefrom into and through the contact chamber, the mixer and the detector. All of this is followed by a fifteen minute regeneration period during which solvent from tank 12, bypassing the sample loop as previously described, flows through the contact chamber to release bound antigens thereby regenerating the immunoadsorbent. The released antigens are subjected to detection as they move through the flow cell to eventual discard.

In other tests, the cycle time has been reduced to less than fifteen minutes. In general, the cycle time can be reduced by increasing the concentration of radioactive tracer.

As noted, a suitable reagent for regeneration of the immunoadsorbent is one which will break the bond between the antigen and antibody but does not adversely affect the antibody. That is, it does not loosen it from its support nor reduce either its permeability of or affinity for antigen. So far identification of suitable reagents has been empirical on the basis of behavior. However, once a suitable reagent for a given antibody-antigen system has been identified, it becomes a permanent reagent for that system.

Thus, the unexpected discovery that regeneration is possible and the identification of suitable reagents makes possible rapid analysis at greatly reduced costs. Moreover, the system is capable of automation thereby reducing human error with a concomitant increase in accuracy.

Throughout the specification reference has been made to bound antigen. This refers to the antigen bound to the antibody mass. The bound antigen is measured only after it has been released from the antibody by the regenerating solvent. If the percent recovery of bound (released) antigen is added to the percent of free antigen measured in any cycle, the total is consistently at 100% for practical purposes. This is significant because it confirms that substantially all bound antigen is released from the antibody and that the antibody is completely regenerated.

Although the invention has been described with particular reference to steroids, it is not intended to be so limited as it has been used with systems for the determination of polypeptides, thyroid hormones and some viruses. It is clear then, that the invention has broad application to radioimmunoassay procedures.

Typical of the materials which may be quantitatively determined by the system of the present invention are the following: estriol, digoxin, digitoxin, testosterone, estradiol, aldosterone, progesterone, cortisol, 11-desoxycortiosterone, 11-desoxycortisol, thyroid hormones such as thyroxin ($T_4$), triiodothyronine ($T_3$), polypeptides such as angiotensin, TSH (thyroid stimulating hormone), ACTH, GH (growth hormone), HPL (human placento-lactogen), parathormone, calcitonin, insulin, glucagen, polypeptide proteins such as CEA (carcino embrionic antigen), alphafetoprotein, interferon, viruses such as Australia antigen, vitamins such as D and $B_{12}$, folic acid and drugs such as dilantin and barbiturates, to mention only a few.

The apparatus of this invention provides not only a fast assay but one as reliable as the classic assay systems. For example, estriol assays are routinely completed in nine minutes by the system of this invention as compared to two hours for the classic methods. The apparatus of this invention is also capable of providing assays of nano- and picogram quantities. The data produced by the apparatus of this invention compares favorably with that obtained by classical methods, i.e. a standard deviation of between 5% to 6%.

More particularly, the improved apparatus of the present invention is designed to carry out several functions in a relatively simple and efficient manner. Generally, as already described, the unit basically includes an interval timer which controls timed functions of eight different sequential operations of the machine. Thus, referring to FIG. 2a, an apparatus is shown which performs the same general function as that already described, but of simpler construction. As shown the apparatus includes an interval timer 50 which controls various pumps and valves which operate to control flow of reagents and reactants. The timer may be variable from 0.01 to 9.99 minutes to increments of 0.01 minutes for each of the eight periods or sequences of machine operation.

Figure 2A:
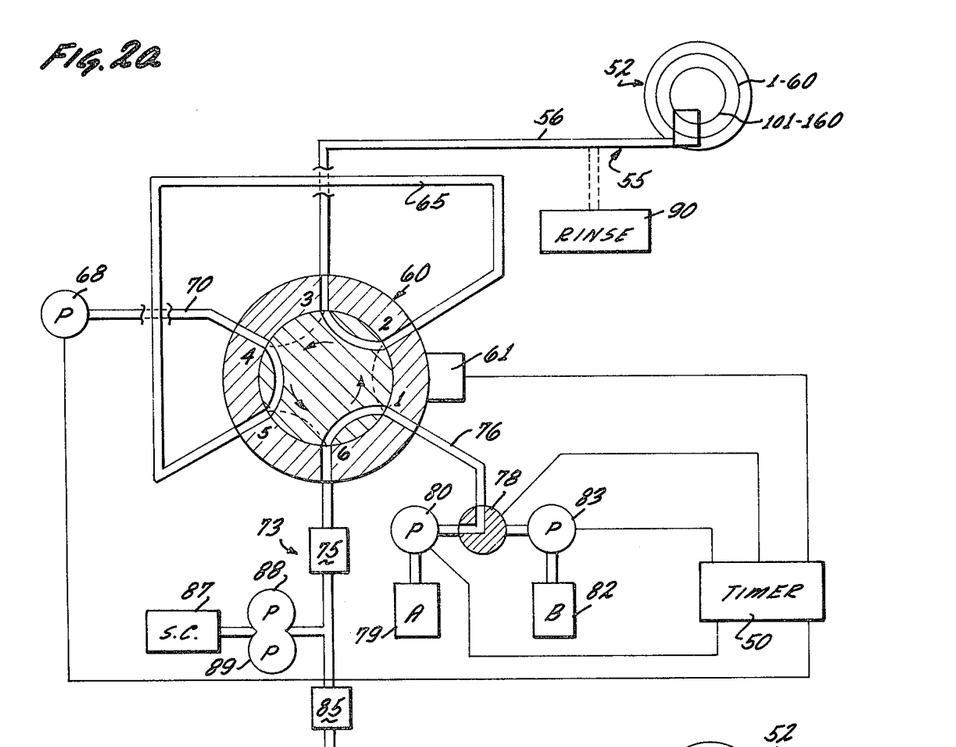
FIGS. 2a and 2b are diagrammatic views of a modified form of the apparatus of the present invention.

The apparatus includes a sample carousel 52 cooperating with an aspirator mechanism 55. The carousel includes 120 chambers arranged in an inner and outer circle of 60 chambers each, the outer being numbered 1–60 and the inner from 101 to 160 so that the electronic control equipment may more easily identify the samples. Thus, in a typical operation, the equipment may run 120 test on estradiol. The samples are collected and identified in the usual manner and a log maintained of which sample is placed in that chamber. Less than all chambers may be used, but since the equipment is designed for automatic assay, it is intended that a significant number of assays be run for each test series.

The aspirator automatically and sequentially samples the outer ring and then advances to the inner ring as the carousel is indexed from position 60, the last of the outer ring chambers, to 101, the first of the inner ring chambers. The chambers of the two rings are staggered such that the chamber 101 is located radially inwardly of outer ring chambers 59 and 60 and between the two.

The aspiration mechanism is connected by conduit 56 to a six valve 60 made of three staggered sets of communicating ports and three staggered sets of blind ports. As shown in FIG. 2a, the blind ports are 1-2, 3-4, 5-6 while the communicating ports are 2-3, 4-5, 6-1. Thus, by indexing the movable valve head, various ports may be placed in communication with various conduits or isolated from various conduits as needed to accomplish machine sequence. A head is indexed relative to the body by control 61 which in turn may be controlled by the interval timer 50 or other timer as provided in the unit, as long as operation is synchronized for the sequence of operation.

A sample loop 65 is connected to ports 2 and 5 of the valve body while aspirator conduit is connected to port 3. Sample pump 68 is connected to port 4 through conduit 70, the pump being controlled by timer 50. Connected at port 6 of the valve is the flow stream system 73 which includes the contact chamber holder 75 which may be as already described in connection with 16 of FIG. 1.

A preferred chamber holder 75 is that described in application Ser. No. 565,848, filed Apr. 7, 1975, and assigned to the same assignee, whose disclosure is incorporated herein by reference.

Connected to port 1 of the valve 60 is a buffer conduit 76, controlled by valve 78 which permits flow from buffer A, 79, as controlled by pump 80, or buffer B, 82, as controlled by pump 83. Each of pumps 80 and 83 as well as valve 78 are controlled by the timer 50.

Downstream of the chamber holder 75 is a detector 85 with a source of scintillation coctail 87 being joined to the line and controlled by dual pumps 88, 89, the flow stream system emptying the waste, as indicated.

Each of the pumps 68, 80, 83, 88 and 89 is operated digitally and provides pump rates of from 0.01 ml/min to 9.99 ml/min. These pumps may be of the piston driven type, are filled by aspiration as the piston moves up and empty as the piston goes down. Pump speeds are controlled digitally, and the valves and pumps operate according to signals from the timer 50.

The detector 85 is a dual bialkali liquid scintillation detector, enclosed in a lead shield. Signals from the detector are sent to a pulse height analyzer for evaluation of coincidence prior to counting.

Overall, the apparatus described includes an immobilized immunoadsorbent within the chamber holder 75 consisting of antibodies attached to a solid support matrix. The pumps and valves control passage of the antigen mixture containing tracer labelled antigen through the chamber 75. The free antigen not bound to the antibody is eluted with buffer and counted as free. The bound antigen is then eluted with appropriate eluting agents and subsequently counted in a continuously moving flow stream. This allows counting of both free and bound antigen and the determination of the bound antigen to the antibody. It also allows correction of losses due to the extraction of antigens from plasma.

Figure 2B:
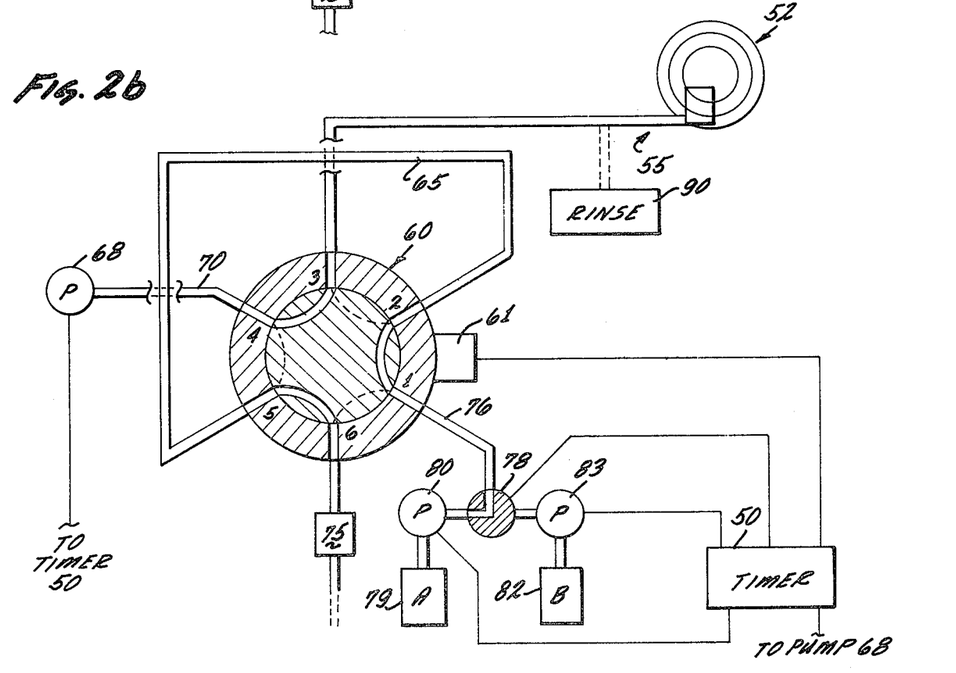

Referring to FIG. 2b, wherein the same reference numerals have been used, where applicable, valve 60 has switched to a position in which conduit 56 is now connected to pump 68 while the sample loop 65 is connected to the buffer system and the flow stream system 73.

Basically, the apparatus sequentially and in a controlled manner proceeds automatically through a series of operations, identified as periods 0 to 7, for illustrative purposes. The sequence generally is as follows: during period 0, the first sample in sample carousel is aspirated into the constant volume loop. In period 1, the first sample is introduced into the flow stream, which continues to the end of period 3. In period 4 the sample loop and the aspirator is rinsed in preparation for a new sample and buffer is flowed into the flow stream to elute the bound antigen. During period 5, the sample aspirator pump 68 is filled with rinse water for the next cycle and elution of the bound antigen continues, the latter extending to the end of period 6. During period 5 the carousel is indexed to the next sample. During period 7 the aspirator tube enters the next sample while buffer rinses out the flow stream. At the end of period 7 the cycle starts again at period 0.

Referring now to FIGS. 2a and 2b, the details of the system sequence may be understood. As illustrated in FIG. 2a, valve 60 is positioned such that conduit 56 is interconnected to the sample loop 65 and to the sample pump 68 through conduit 70 and internal ports 4–5.

The buffer system is interconnected through port 1–6 to the flow system 73. The relative position of valve 60 illustrated in FIG. 2a is the position the valve occupies during periods 0 and 4 through 7 inclusive. In periods 1–3, valve 60 is in the relative position illustrated in FIG. 2b with the sample loop in series with the flow stream 73, while the aspirating loop is isolated.

The sample loop 65, in accordance with the present invention is of a preset volume of between 0.2 to 0.5 milliliters, while the pumps have an internal volume of 0.1 milliliter. As will be appreciated, the antigen samples being analyzed are relatively small, and the amount of antigen being determined quantitatively by the equipment of the present invention is in the nano- and picogram quantity level.

Referring again to FIG. 2a, at the start of period 0, the aspirator tube is already in contact with the sample, this operation having taken place in the preceding period 7. Under the control of the timer 50, pump 68 is energized to withdraw the sample from the sample holder positioned within the carousel to initiate introduction of the sample into the sample loop 65 of predetermined volume. At the same time, timer 50 positions valve 78 and actuates pump 80 such that buffer A is pumped into conduit 76, internally through ports 1–6 of valve 60 into the flow stream system 73, and through the chamber 75 in order to rinse the chamber with A buffer. The A buffer, whose composition has already been identified, by way of example, constitutes a rinse buffer.

The length of time of period 0 or any other period may vary depending upon the antigen involved in the assay and the size of the unknown sample which is being processed. Since the equipment herein described may be used for assay of different antigens, in each series of assays, the variable time feature of the timer permits considerable latitude in the length of time for each of the steps in the sequence, that is, periods 0 through 7. Normally, the length of time of each of the periods involved in the sequence depends upon the particular antigen being assayed, and the particular desires of the machine operator, although the usual length of time for a sequence from period 0 through period 7 is in the order of 5 to 12 minutes depending upon the particular antigen being assayed.

At the end of period 0, valve 60 is switched to the relative position illustrated in FIG. 2b. During period 1, the sample in the loop 65 is introduced into the flow stream 73. At the same time, there is a delay for the "free" counts to reach the detector. During this period, the sample identification is ascertained and stored in the computer to be described hereinafter which forms part of this apparatus.

Period 2, in which valve 60 is in the position illustrated in FIG. 2b involves a continuation of the introduction of the sample into the flow stream and at the end of period 2, the A buffer system continues to introduce A buffer through conduit 76 which is now connected to the sample loop through ports 1–2, and the sample loop is rinsed with rinse buffer. During period 3, the sample is flowed into the flow stream.

At the start of period 4, valve 60 is operated to remove the sample loop 65 from the flow stream 73 to a rinse position, as illustrated in FIG. 2a. During this same period, buffer B system is energized by switching the position of valve 78, and energizing pump 83 through the timer 50 to introduce eluting buffer, buffer B, into conduit 76 which, through ports 1–6 of valve 60, is now interconnected to the flow stream 73. The eluting buffer operates to release bound antigen from the immobilized antibody. At the same time, the pump on the buffer A system is filled with the A buffer.

Period 4 also includes rinsing the sample loop 65 and aspirator system with rinse solution, normally water, by emptying of the sample pump. This is accomplished by swinging the aspirator head to the dotted line position indicated in FIG. 2a such that the aspirator head is over a waste receptacle 90. Pump 68 is energized by the timer 50 to pass rinse water through the sample loop and through the aspirator head thereby rinsing the loop in preparation for the receipt of another sample. During the rinsing operation, and as part of the period 4, the last of the free antigen counts reach the detector. At the end of the period of free counts are transferred to the computer and the counters are reset.

At the start of period 5, the B buffer reaches the antibody chamber and starts the elution procedure. At the same time during this period, the carousel is advanced to the next position, while the sample pump is partially filled with rinse solution. Period 6 involves the continuation of the elution of the bound antigen with buffer B as described.

At the end of period 6, and at the start of period 7, a buffer is then introduced into the flow stream as a rinse solution for the B buffer, while the pump of B buffer is filled with buffer B. Also, the sample aspirator tube is lowered into the next sample cup in preparation for the next cycle. During period 7, the counts of bound antigen are transferred to the computer.

The data from the detector is fed to a computer which has been programmed in accordance with data received from standard solutions. Preliminary programming of the computer for a run is accomplished through a high speed Victor printer and keyboard for computer input, the printer being coupled to the computer in the usual manner.

The standardization procedure includes standardizing with the standard curve samples which is accomplished by running a background sample containing no radioactivity, a 0 sample containing the radioactive tracer only, and up to 20 known standards. The percent binding for 0, the standards and the unknown samples are computed from the net free and bound counts. The net total count is computed and printed for the standards. The percent binding is also printed and once the last standard has been run, the mean and the coefficient of variation for the total counts of all standards are printed, that is, from the computer.

An initial least squares logit plot is computed from the log of the antigen concentration and the logit of the percent binding for the standards. The results of the logit plot are tabulated with "$x$" value of the standard, "logit $y$", and the calculated "$x$" value from the logit plot. The slope intercepts, correlation coefficient and N, the number of standards for the plot are printed. An improved logit plot is calculated assuming the percent binding of the zero tracer used to compute the initial plot may not represent the best value. Therefore, the percent binding of the zero is increased incrementally and the plot recomputed until the correlation coefficient no longer improves. The revised logit "$y$" values and the calculated "$x$" values from the resulting curve are tabulated as well as the new slope, intercept, correlation coefficient, and N. Since there also can be some non-specific binding to the solid support, the percent binding to the solid support, the percent binding at maximum possible antigen concentration is also modified in an iterative manner. The result of this third set of calculations are also summarized for the ng/ml of the standard the "logit $y$" and the computed concentration of the antigen from the improved plot. The resulting slope intercept, correlation coefficient and N are again summarized as well as the final percent binding for the 0 tracer and the percent binding for maximum displacement of antigen from antibody.

The computer used with the equipment of the present invention may be for example a DCC D-116 computer with a 16K memory.

As will be appreciated from the above description, the apparatus of the present invention represents a relatively simple and efficient device for the rapid quantitative determination of an antigen by radioimmunoassay. By the provision of a reusable immobilzed immunoadsorbent, an automatic system is provided for the assay. By changing the contact chamber and the immunoadsorbent, one may use the same equipment for assay of the antigens noted. For example, estriol may be run in one series, the chamber changed and estradiol or $T_3$ or $T_4$ in the subsequent series.

It will also be appreciated that the cycle sequence may be varied. For example, rinsing of the sample loop 65 may not be needed while one may wish to rinse the aspiration tube. This may be achieved by operating the sample aspiration pump 68 during period 2 or 3 instead of period 4. Another variation may involve clearing the sample loop 65 or the aspiration tube 56 of rinse solution. This may be accomplished by aspirating air into the tube after rinsing.

Gamma radiation from $I^{125}$ may be counted using the liquid scintillator and the photomultiplier tubes or by using a gamma detector. When a gamma detector is used, there is no need to use the scintillation cocktail. In this latter case, a solution of sodium hypochlorite is used in the liquid scintillation cocktail pumps and the hypochlorite oxidizes the organically bound radioactive Iodine to prevent it from binding to the tubing in the detector since such binding causes an increase in background counts during a run. Thus, the relative rate of these pumps may be slower when pumping the sodium hypochlorite than when pumping the scintillation cocktail.

Figure 3A:
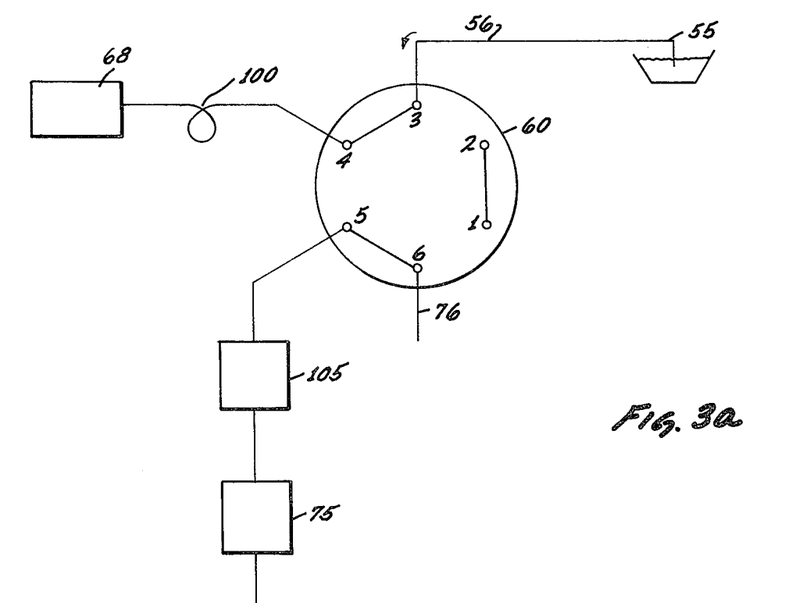
FIGS. 3a and 3b are diagrammatic views of a modified form of the apparatus shown in FIGS. 2a and 2b.

As a further indication of alternate modes of operation, reference is made to FIG. 3a wherein like reference numerals have been used, the valve 60 is shown in a relative position indicated in FIG. 2b, ports 1 and 2 of the valve being blocked. The buffer system is connected at port 6 through conduit 76. The aspirator 55 is connected to port 3 through conduit 56 while the aspirator pump 68 is connected to port 4 by a holding tube 100 into which the sample is aspirated and held. In this relative position of the valve 60, the buffer system is connected to the contact chamber 75 through conduit 76, port 6 and port 5, as shown. A prefilter 105 is located upstream of the chamber to collect any solids which may be in the system, thus protecting the contact chamber. In this form, the holding tube functions as a sample loop.

Figure 3B:
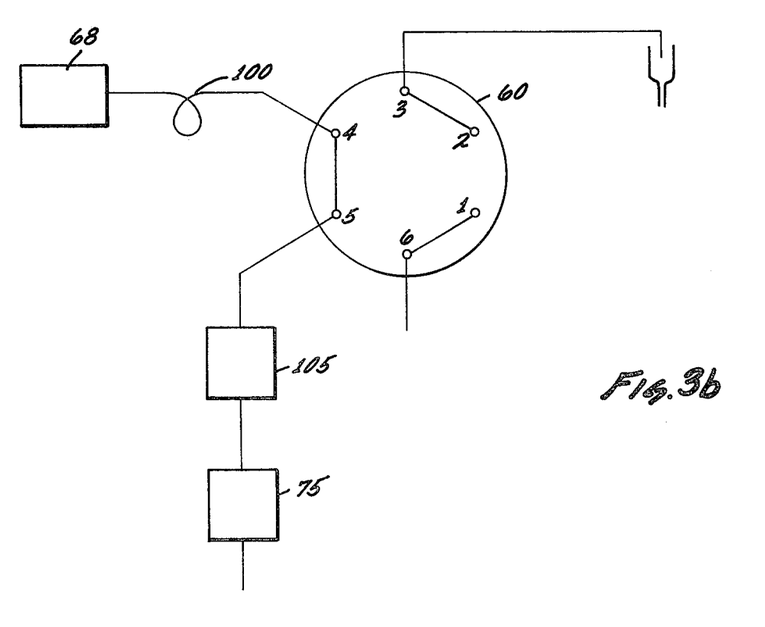

By switching the valve 60 to the position illustrated in FIG. 3b, corresponding to the relative position of FIG. 2a, by the control mechanism described, the buffer system is blocked off through blocked port 1 while the aspirator line 56 is connected to blocked port 2. The aspirator pump 68 is reversed emptying the holding loop 100 into the contact chamber 75 through the prefilter 105. Thereafter, the valve is switched to the relative position of FIG. 3a.

Prefilter 105 may also be used in the arragement shown in FIGS. 2a and 2b between port 6 of valve 60 and contact chamber 75. The prefilter includes a housing which forms a chamber filled with discs of Teflon felt held between spaced 400 mesh nylon discs at each end. The nylon discs are held in place by end pieces received in the housing. The prefilter functions to extend the life of the contact chamber and improve the reproducibility of the chamber.

It will be apparent to those skilled in the art that various alterations, changes and modifications may be made without departing from the spirit and scope of the invention as set forth in the appended claims.

I claim:

1. Apparatus for automated radioimmunoassay comprising:
   means for holding at least one antigen sample to be analyzed,
   means forming a contact chamber through which said samples are flowed,
   immobilized immunoadsorbent means positioned within said chamber,
   said immunoadsorbent including a particulate material having chemically bound thereto an antibody specific to the antigen in said sample and for forming a fraction bound to said antibody and an unbound fraction which passes through said chamber,
   means forming a storage for eluant solution,
   flow line means for flow of fluid to and from said contact chamber,
   means for detecting radioactive impulses positioned to receive impulses of a radioactive material from at least one of said bound and unbound fractions in said flow line means,
   means for directing flow of an antigen sample and a radioactive labelled antigen into said contact chamber to form said bound and unbound fraction,
   means to direct flow through said contact chamber of solvent to effect stoichiometric release of the antigens bound to said immobilized immunoadsorbent to form a released bound fraction
   means to effect flow sequentially of successive antigen samples throuch said contact chamber for assay thereof and to effect flow of eluant solution through said chamber subsequent to flow of each said antigen sample; and said detecting means being operative to receive impulses from one or both of said unbound fractions and said released bound fraction passing through said flow line means.

2. Apparatus as set forth in claim 1 wherein said immobilized immunoadsorbent comprises a mass of particulate solids to which antibodies are covalently bound.

3. Apparatus as set forth in claim 1 further including means to support a plurality of antigen samples to be analyzed.

4. Apparatus as set forth in claim 1 further including means to introduce a scintillation material into the material flowing out of said contact chamber prior to flow of said material to said means for detecting.

5. Apparatus as set forth in claim 1 further including means forming a sample loop, means to selectively interconnect said sample loop to said means for flowing an antigen sample into said contact chamber.

6. Apparatus as set forth in claim 5 wherein said sample loop is of a predetermined volume.

7. Apparatus as set forth in claim 1 further including means forming a rinse system to rinse said contact chamber subsequent to flow therethrough of said solvent.

8. Apparatus as set forth in claim 1 further including means forming a timer to control flow of components in a predetermined sequence.

9. Apparatus for radioimmunoassay comprising:
a contact chamber located in a liquid flow line,
a mass of antibodies specific to an antigen to be detected, said antibodies being chemically bound to a mass of particulate solids,
means supporting said antibodies as an immobilized mass of particulate solids in said contact chamber whereby liquid flows through said mass,
means for holding a rinse solution,
means for holding an eluant solution,
means for flowing a predetermined volume of antigen sample and radioactive labelled antigen into said contact chamber,
a detector in said flow line downstream from said contact chamber, said detector being adapted to detect radioactive impulses of radioactive material in liquid flowing therethrough, and
means for directing sequentially through said flow line to pass successively through said contact chamber and said detector (a) a rinse solution, (b) a antigen bearing sample and (c) an eluant solution adapted upon passage through said contact chamber to effect release from said immobilized mass of antigens bonded thereto.

10. Apparatus according to claim 9 in which said mass of antibodies comprises a plurality of small solid beads to which antibodies are covalently bonded and said means supporting said antibodies as an immobilized mass comprises a screen transverse to said flow line and on which said beads are retained as a porous mass.

11. Apparatus for radioimmunoassay comprising
means for holding a plurality of antigen samples to be analyzed to determine the quantity of antigen therein, means forming a contact chamber through which each of said antigen samples is passed in predetermined sequence, means in said contact chamber including a matrix having covalently bonded thereto a mass of immobilized antibodies specific to the antigen being analyzed, means for detecting radioactive impulses positioned to receive impulses from the flow of material leaving said contact chamber, means forming a sample loop to receive said antigen samples, means forming a buffer system selectively connected to said sample loop and to said contact chamber, said buffer system including a rinse buffer and an eluting buffer, the latter operative to release antigen bond to the antibodies in said contact chamber, means to transfer said antigen samples to said sample loop, and timer means operative to control introduction of a sample into said sample loop and thereafter to control introduction of said sample into said chamber holder followed by flow of the elution buffer and rinse buffer through said chamber.

12. Apparatus as set forth in claim 11 wherein said detector is a beta detector.

13. Apparatus as set forth in claim 11 wherein said detector is a gamma detector.

14. Apparatus as set forth in claim 11 further including means forming an aspirator system for withdrawing a predetermined antigen sample from said holding means and effecting flow of said sample into said sample loop.

15. Apparatus as set forth in claim 14 further including a rinse system to rinse said aspirator system subsequent to flow of a sample into said sample loop and prior to withdrawal of another sample.

16. Apparatus as set forth in claim 11 further including means forming a multiple port valve, said buffer system and said contact chamber being in fluid communication with selected ports of said valve, and said valve being operative in one position thereof to permit flow of said sample into said sample loop and to permit flow of a portion of said buffer into and through said contact chamber, and operative in another position to permit flow of fluid from said sample loop into said contact chamber.

17. Apparatus as set forth in claim 11 wherein said buffer system includes separate pump means controlling the flow of each of said buffers.

18. Apparatus as set forth in claim 11 wherein said detector means includes means to contact introduce a scintillation material into contact with the portion of the antigen material leaving said contact chamber.

19. Apparatus as set forth in claim 11 wherein said sample loop is of a predetermined volume.

20. Apparatus as set forth in claim 11 wherein said timer is adjustable whereby the period of flow of the elements controlled by the timer may be varied.

21. Apparatus as set forth in claim 17 wherein said pump means is adjustable to vary the volume rate output thereof.

22. Apparatus as set forth in claim 11 wherein said means for detecting includes a dual bialkali liquid scintillation detector, and said detector being provided with a radiation shield.

* * * * *